United States Patent [19]

Keusch et al.

[11] Patent Number: 4,777,954
[45] Date of Patent: * Oct. 18, 1988

[54] CONDUCTIVE ADHESIVE MEDICAL ELECTRODE ASSEMBLIES

[75] Inventors: Preston Keusch, New York, N.Y.; John L. Essmyer, Hasbrouck Heights, N.J.

[73] Assignee: Nepera Inc., Harriman, N.Y.

[*] Notice: The portion of the term of this patent subsequent to Nov. 17, 2004 has been disclaimed.

[21] Appl. No.: 66,661

[22] Filed: Jun. 26, 1987

Related U.S. Application Data

[63] Continuation-in-part of Ser. No. 879,877, Jun. 30, 1986, Pat. No. 4,706,680.

[51] Int. Cl.$^4$ .......................... A61B 5/04; A61N 1/04
[52] U.S. Cl. ..................... 128/640; 128/641; 128/798; 128/802
[58] Field of Search .............. 128/639–641, 128/798, 802, 803; 604/20, 290; 252/500

[56] References Cited

U.S. PATENT DOCUMENTS

| | | | |
|---|---|---|---|
| 3,419,006 | 12/1968 | King | 604/290 |
| 3,685,645 | 8/1972 | Kawaguchi | 128/803 X |
| 3,993,049 | 11/1976 | Kater | 128/641 |
| 4,367,745 | 1/1983 | Welage | 128/798 X |
| 4,474,570 | 10/1984 | Ariura et al. | 604/20 |
| 4,706,680 | 11/1987 | Keusch et al. | 128/640 |

FOREIGN PATENT DOCUMENTS

| | | | |
|---|---|---|---|
| 57-49431 | 3/1982 | Japan | 128/639 |
| 1251861 | 8/1986 | U.S.S.R. | 128/639 |

Primary Examiner—Lee S. Cohen
Attorney, Agent, or Firm—Millen & White

[57] ABSTRACT

A medical electrode adapted for providing electrical contact with a patient's skin and comprising:
(a) a conductive member including means for connecting the medical electrode to an external electrical apparatus; and
(b) interfacing means comprising a solid sheet of a conductive viscoelastic hydrophilic gel consisting essentially of
  (i) water;
  (ii) a water soluble magnesium or calcium salt; and
  (iii) an amount dispersed uniformly throughout the water of from about 2 to 35 wt % of a cross-linked polyethylene oxide, effective to form with the water a tacky surface viscoelastic adhesive solid;

which hydrophilic gel is produced by subjecting a liquid film of an aqueous solution of the water soluble salt and a linear water soluble polyethylene oxide having a weight average molecular weight from about $0.05-10 \times 10^6$ Daltons to an amount of high energy radiation effective to convert the liquid film to a sheet of adhesive viscoelastic solid.

11 Claims, 2 Drawing Sheets

CONDUCTIVE ADHESIVE MEDICAL ELECTRODE ASSEMBLIES

CROSS-REFERENCE TO RELATED APPLICATION

This is a continuation-in-part of Ser. No. 879,877, filed June 30, 1986, now U.S. Pat. No. 4,706,680.

BACKGROUND OF THE INVENTION

This invention relates to conductive adhesive medical electrode assemblies adapted for application adhesively to the skin to provide electrical contact therewith.

This application is related to concurrently filed application Ser. No. 879,876, filed June 30, 1986, whose disclosure is incorporated herein by reference, which claims a sheet of the hydrophilic gel in conductive form employed as a conductive member interfacing with the skin of a patient in the medical electrode assemblies of this invention to provide electrical contact therewith.

Medical electrodes comprising, as a conductive member interfacing with the skin of a patient, a sheet or film of a hydrophilic gel are well known in the art. Hydrogel sheets adapted for use in medical electrode-related applications are commercially produced by Promeon, a Division of Medtronic, Inc. (Brooklyn Center, Minn.); Valleylabs, Inc., a Division of Pfizer (Boulder, Colo.) Biostim, Inc. (Princeton, N.J.); Lectec Corp. (Eden Prairie, Minn.); and Conmed (Utica, N.M.).

Numerous U.S. patents disclose hydrophilic gels and medical electrodes employing them. The following illustrate the early state of that prior art.

U.S. Pat. No. 3,357,930 (electrically conductive transparent films comprising a polymeric matrix in gel form, a plasticizer therefor, an ionized electrolyte soluble in the plasticizer, and an ionizable solvent, e.g., solid polyvinyl alcohol, glycerine, lithium chloride and silica).

U.S. Pat. No. 3,911,906 (electrode with skin interfacing film of a pressure sensitive adhesive containing fine electrically conductive particles, e.g., an acrylic copolymer containing carbon powder).

U.S. Pat. No. 3,993,049 (electrode comprising a pliant patch of a formaminated material covered on the side adapted to be placed on the skin with a salt-containing adhesive).

U.S. Pat. No. 3,994,302 (stimulating electrode in which the skin contacting element is an ion-exchange material, e.g., a vinyl pyridine grafted to a polyethylene base).

U.S. Pat. No. 3,998,215 claims an electrically conductive pad which employs a hydrogel impregnated with a fibrous carrier. The polymers disclosed herein as operable require a chemical cross-linking agent. The commercial version thereof sold by the patentee (Minnesota Mining and Manufacturing Co.) has poor skin adhesion and contains bubbles (the latter presumably due to the viscosity of the starting gel and/or the technique employed to impregnate the fibrous carrier with the starting polymer solution). Bubbles in the conductive pad are undesirable because they create local areas of altered electrical properties.

Since the issuance of U.S. Pat. No. 3,998,215, numerous other patents employing a hydrophilic gel as an electrically conducting means which interfaces with the skin of the patient have issued. The following are illustrative of such patents.

U.S. Pat. No. 4,008,721 (tape electrode comprising a skin-contacting layer of adhesive material, e.g., acrylic copolymer).

U.S. Pat. No. 4,054,714 (electrically conductive adhesive useful for binding together surfaces of electronic devices, comprising a polymeric binder, conductive particles whose surfaces are a noble metal and a normally liquid polyhydric alcohol).

U.S. Pat. No. 4,067,342 (tape electrode for transmission of electrical signals into the body through the skin employing a tape having a surface of a conductive material combined with an adhesive e.g., acrylic polymer adhesive, and a second surface with the conductive material comprising a magnetic substance.)

U.S. Pat. No. 4,094,822 (electrode having a cup, which is taped to the skin, containing a semi-solid adhesive polymeric material, e.g., a mixture of polyvinyl alcohol, boric acid, CMC, glycerol and water and an electrolyte, e.g., AgCl or a zinc salt).

U.S. Pat. No. 4,066,078 (electrode with a skin interfacing film having adhesive, plastic and hydrophilic properties, e.g., produced from an interpolymer comprising (a) 10–90 parts of an ester of an $\alpha,\beta$-olefinically unsaturated carboxylic acid and a mono- or polyhydric alcohol; (b) 90–10 parts of an $\alpha,\beta$-olefinically unsaturated comonomer; and (c) at least 0.02 parts of a cross-linking agent comprising a difunctional monomer.)

U.S. Pat. No. 4,092,985 (disposable electrode comprising an elastically stretchable layer of water permeable porous webbing permeated with a high water content liquid or semisolid conductive medium).

U.S. Pat. No. 4,109,648 (electrode assembly comprising a self-supporting body of hydrogel, e.g., hydroxyethyl methacrylate polymerized with ammonium persulfate and sodium metabisulphite around graphite fiber).

U.S. Pat. No. 4,125,110; U.S. Pat. No. Re. 31,454 (electrode comprising as a skin interfacing substrate, a colloidal dispersion of a naturally occuring hydrophilic polysaccharide such as karaya, and a salt in an alcohol as a continuous phase).

U.S. Pat. No. 4,141,366 (electrode for transmitting electrical signals through the skin employing a normally "dry" adhesive which is activated at the time of application by a suitable solvent).

U.S. Pat. No. 4,273,135 (an essentially dry electrode employing as the conductive interface a cohesive, conformable, nonionic hydrophilic synthetic polymer plasticized with a monomer, e.g., glycerol. The electrode is applied to abraded skin wet with normal saline solution or water). This patent contains a detailed description of prior art electrodes in addition to those described and claimed (herein).

U.S. Pat. No. 4,274,420 (an electrode similar to U.S. Pat. No. 4,125,110 in which the adhesive substrate comprises a karaya gum matrix supporting an electrically conductive fluid).

U.S. Pat. No. 4,300,575 (an electrode with a conductive element composed of karaya, carbon black, isopropyl alcohol and karaya gum conductive solution).

U.S. Pat. Nos. 4,317,278; 4,318,746 and 4,362,165 electrodes comprising an annulus of foam with an electrode gel in the central region of the annulus, which gel is the subject of U.S. Pat. No. 4,318,746 and is composed of two polymers, one of which is hot water soluble, e.g., kappa carrageenan, and the other is not, e.g., hydroxypropylmethylcellulose, and which contains a potassium salt to enhance the gel's conductivity.

U.S. Pat. Nos. 4,365,634; 4,393,584; and 4,522,211 (electrodes with adhesive layer secured to a semi-flexible plastic-like sheet, and formed from a known electrically conductive adhesive, e.g., Johnson & Johnson Co.'s "Bioadhesive", disclosed in U.S. Pat. No. 4,066,078, or in U.S. Pat. Nos. 4,008,721; 3,998,215; 3,993,049; and 3,911,906; preferably a hydrophilic material disclosed in U.S. Pat. Nos. 3,822,238, 4,156,066 and 4,156,067).

U.S. Pat. No. 4,383,529 (iontophoretic electrode device with a semi-solid hydrophilic hydrated gel formed, e.g., from agar, a protein or a synthetic polymer, e.g., methyl cellulose).

U.S. Pat. No. 4,458,696 (TENS electrode with an extensible interfacing layer of up to 10 mils thickeners comprised of a carrier portion coated with an electrically conductive adhesive, preferably a 75:25 butyl acrylate-acrylic acid copolymer neutralized with methyl diethanolamine to which are added a water-soluble plasticizer and tackifier, as described in U.S. Pat. No. 3,065,770).

U.S. Pat. No. 4,515,162 (electrode pad comprising a tacky crosslinked hydrogel adhered to an electrode terminal plate, e.g., a polyacrylic acid and a polyacrylic acid salt, water, and a compound containing at least two epoxy groups, as cross-linking component, and optionally a tackifier, e.g., glycerine, propylene glycol or polyethylene glycol, an electrolyte material, e.g., sodium chloride or potassium chloride, a pH controlling agent, a flexibility imparting agent, an antifungal agent, and the like).

U.S. Pat. No. 4,524,087 (electrode with a conductive adhesive thereon which is swellable, dermally-nonirritating conformable, coadhesive, ionic hydrophilic polymer, e.g., produced by UV polymerizing a mixture consisting of triethyleneglycol-bis-methacrylate dissolved in acrylate acid to which is added glycerol and potassium hydroxide in water, using a free radical initiator to initiate polymerization, e.g., a photoinitiator).

U.S. Pat. No. 4,543,958 (electrodes with conductive adhesive film comprising a naturally occurring karaya gum, e.g., available in sheet form from Lectec Corp. or as described in U.S. Pat. Nos. 3,357,930; 3,993,049; 4,066,078; and 4,141,366).

The preferred hydrophilic gels of this invention fall within the broad class of cross-linked polyethylene oxide polymers described in U.S. Pat. Nos. 3,264,202 and 3,419,006. See also U.S. Pat. Nos. 3,898,143; 3,993,551; 3,993,552; 3,993,553 and 3,900,378.

Although there exists in the prior art numerous teachings of medical electrodes having a hydrophilic gel as a skin interfacing member, none meet all the criteria of an optimum medical electrode, i.e., a dermatologically inert skin interfacing member, i.e., one which contains no organic solvents, residual monomer chemical cross-linking agents or substantial quantities of uncrosslinked adhesive polymer; it is a viscoelastic solid, i.e., it readily conforms to non-flat areas of the skin; it is sufficiently adhesive to adhere firmly to the skin, so that there is little likelihood of it falling off during use, yet it is not so adhesive that it causes pain and/or damage to the skin upon removal; it is adequately adhesive to moist as well as to dry skin and to soiled as well as to clean skin, so that skin pre-preparation with organic solvent or abrasive is not required; it has superior electrical properties, such as low impedance and low offsets; it has a good shelf life in its unopened package; and its properties do not readily deteriorate between the time the package in which the electrode is sealed is opened and before or during use. The medical electrodes of this invention possess all of these and other advantageous properties for long term use.

OBJECTS OF THE INVENTION

It is an object of the invention to provide medical electrodes employing as a skin interfacing conductive member a hydrophilic gel which consists substantially of water, a cross-linked homopolymer and an electrolyte.

It is another object to provide such an electrode in whose hydrophilic gel is biologically inert.

It is another object to provide such an electrode which adheres to the skin when affixed thereto without the necessity of skin pre-preparation, e.g., abrasion or wetting the skin and/or drying with solvent.

It is a further object to provide such an electrode whose adherence to the skin is not adversely affected by the presence of normal amounts of moisture on the skin.

It is a further object to provide such an electrode with superior and stable electrical properties, which is suitable for long term use and which can be peeled off the skin after use without damage to the skin and without having a noticeable residue.

It is a further object to provide such an electrode whose hydrophilic gel is free of leachable ingredients, e.g., monomers, plasticizers, cross-linking agents, tackifiers, etc.

It is a further object to provide such an electrode which does not readily lose its water content upon exposure to ambient atmosphere.

It is a further object to provide methods for transmitting electrical signals from the skin or electrical energy to the skin employing a medical electrode of this invention.

Other objects will be apparent to those skilled in the art to which this invention pertains.

SUMMARY OF THE INVENTION

In an article of manufacture aspect, this invention relates to a medical electrode adapted for providing electrical contact with a patient's skin and comprising:

(a) a conductive member including means for connecting the medical electrode to an external electrical apparatus; and (b) interfacing means comprising a solid sheet of a conductive hydrophilic gel, connected electrically with the conductive member, for interfacing electrically with and adhesively to the patient's skin, which sheet is more cohesive than it is adhesive to the patient's skin and is mechanically connected more firmly to the conductive member than it can be adhesively affixed to the patient's skin, thereby enabling concurrent removal of the conductive member and the sheet from the skin after use without leaving a noticeable residue on the skin and wherein the hydrophilic gel is a homogeneous aqueous mixture, substantially free of unbound water, monomers and cross-linking agents, of:

(i) water;
(ii) an amount dissolved in the water of a water soluble electrolyte effective to reduce the transverse electrical resistance of the film to an impedance at 60 Hz of less than 1,000 ohms, and
(iii) an amount dispersed uniformly throughout the water from about 2 to 35 wt% of a cross-linked polyethylene oxide, effective to form with the water a tacky surfaced viscoelastic solid, which hydrophilic gel is produced by subjecting a liquid film of an aqueous solution having a viscosity of about $2\text{-}2{,}000\times 10^{-3}$ cps of the electrolyte and a linear water soluble polyethylene oxide having a weight average molecular weight from about $0.05\text{-}10\times 10^6$ Daltons to an amount of high energy radiation effective to convert the liquid film to a sheet of the viscoelastic solid.

In a method of use aspect, this invention relates to a method of transmitting an electrical signal from the skin of a patient employing a medical electrode of this invention.

In another method of use aspect, this invention relates to a method of transmitting an electrical energy to the skin of a patient employing a medical electrode of this invention.

In a method of manufacture aspect, this invention relates to a method of manufacturing a skin interfacing member of a medical electrode of this invention which comprise the steps of subjecting a liquid film of an aqueous solution, having a viscosity of about $2\text{-}2{,}000\times 10^3$ cps, of an electrolyte and about 2 to 35 wt% linear water soluble polyethylene oxide having a weight average molecular weight of about $0.05\text{-}10\times 10^6$ Daltons to an amount of high energy radiation effective to convert the liquid film to a sheet of the viscoelastic adhesive solid and thereafter forming the thus produced film into a skin interfacing member of a medical electrode.

DETAILED DISCUSSION

The hydrophilic gels employed in this invention are unique in that although they are electroconductive, they are substantially free of unbound water. This in an important property for several reasons. First, it means that the gel does not "bleed" free water under the influence of pressure and/or elevated temperatures, which bleeding can adversely affect one or both of adhesiveness and/or uniformity of conductivity. Second, it means the gel is not "broken" if subjected to temperatures below the freezing point of water. This is very important from a storage and shipping stability point of view. Finally, it renders the gel more resistant to "drying out" after being removed from its sealed gas and moisture impermeable package.

Because medical electrodes must be sterile, the packaging of the electrode must ensure such sterility. Although this cannot conveniently be achieved conventionally by autoclaving, since this could adversely affect the polymer or alter the moisture content of the gel, sterility can readily be accomplished by other means, e.g., with ethylene oxide or by packaging the electrode as an integral part of the high energy radiation step of converting the starting liquid polymer solution to a solid hydrogel, which effectively sterilizes the hydrogel and associated structural and packaging materials.

The hydrogels employed in this invention are characterized by being tacky viscoelastic solids which, in the rolling ball tack test described hereinafter, typically give a rolling ball distance of less than about 10 mm and typically give an adhesion energy force in the Adhesion Energy Density Determination Test described hereinafter of about 2 to 80 g-cm/cm$^2$ which adhesive sheets have greater cohesive strength than adhesive strength, whereby the sheet can be removed from a surface to which it is affixed without leaving a visible residue. Their tackiness or stickiness is so pronounced that tactile examination thereof leaves one with the strong impression that a residue should be left on the skin when a sheet of the gel is peeled off therefrom. However, the sheets of gel are integral single structures, much like a film of thermoplastic polymers. Therefore, they have excellent cohesive strengths which prevents material from separating from the sheet when it is peeled off the skin.

The hydrophilic gels are a homogeneous aqueous mixture of water, an electrolyte and a cross-linked polyethylene oxide (PEO). Not only are they substantially or completely free of unbound water, the advantages of which are discussed above, they are substantially or completely free of discrete polymer particles which could settle out or otherwise adversely affect the physical, electrical or chemical properties of the gels.

These cross-linked PEO polymers and the hydrophilic gels produced therefrom by irradiation with high energy radiation are described generically in U.S. Pat. No. 3,264,202 and 3,419,006, whose disclosures are incorporated herein by reference. However, the specific highly sticky or tacky hydrophilic gels employed in this invention are not disclosed therein. Such gels are produced by employing higher concentrations of starting linear PEO polymers than the minimum needed to produce a solid gel and modifying the amount of radiation to which the starting liquid film is subjected. In other words, low solids, high radiation gels are less tacky than high solids and/or low radiation gels produced from the same starting water soluble linear PEO. Therefore, whereas the preferred polymer contents of the gels of U.S. Pat. No. 3,419,006 is between 2 and 6 wt%, those of the gels of this invention are about 2 to 35 wt%, preferably 4–25 wt% and more preferably in the 7–10 wt% range. Whereas the starting linear PEO of the examples of that patent had a molecular weight of $3\times 10^6$ Daltons and was employed at a concentration of 2 wt%, the starting polymers of the Examples of this invention had a molecular weight of either 0.9 or $4\times 10^6$ Daltons and were employed at concentrations of 9 and 4 wt%, respectively. Higher concentration of the lower molecular weight PEO produced a tackier surfaced hydrogel than the lower concentrations. Therefore, although linear PEO's with molecular weights in the range of about $0.05\text{-}10\times 10^6$ Daltons are operable, providing the proper level of irradiation is employed, those having a molecular weight of about 0.2 to $6\times 10^6$ are preferred and of $0.5\text{-}4\times 10^6$ are especially preferred. Similarly, polymer concentrations of 2 to 35 wt% are operable again provided the proper level of irradiation is employed, but 4 to 25 wt% are preferred.

The concept of fabricating a crosslinked adhesive hydrogel electrode is not only limited to the species polyethylene oxide. Any water soluble tacky polymer or co-polymer or blend of polymers which are radiation crosslinkable are capable of forming a crosslinked adhesive hydrogel sheet. Among others, polyvinyl alcohol or polyacrylamide may be utilized in the same way as the polyethylene oxide to yield an adhesive crosslinked hydrogel electrode. Blends as with polyethylene oxide and other polymers or co-polymers may accomplish the same. An example of this is a co-crosslinked mixture of polyethylene oxide and polyvinyl pyrrolidone. In this instance both materials are adhesive polymers. In a more general way, at least one adhesive polymer can be blended with another non-adhesive polymer in an aqueous salt solution giving a crosslinked adhesive hydrogel electrode. An example of this is the blend of polyethylene oxide and carboxymethylcellulose. In a similar mode of application a water soluble tacky crosslinkable polymer can be blended with inert fillers and yield a crosslinked, tacky hydrogel electrode sheet material. In this instance the major requirement is that the tacky crosslinkable polymer must be the continuous phase in the sheet formed which requires the wetting out and complete encapsulation of the inert filler by the initial polymer-salt solution.

U.S. Pat. Nos. 3,898,143, 3,957,607, 3,993,551, 3,993,552 and 3,993,553 describe the co-crosslinking of polyethylene oxide with a diverse variety of other polymers. U.S. Pat. No. 3,900,378 describes the crosslinking of a polymer with an inert filler.

As stated above, the hydrogels employed in this invention are characterized by exceptional surface stickiness while possessing sufficient cohesiveness to maintain structural integrity when being removed from the skin.

The manner in which hydrogel film of this invention adheres to the skin is an important aspect of this invention. The hydrogel adheres quickly and tenaciously to both dry and damp clean and soiled skin. It is extremely tolerant to perspiration which forms from the skin under the hydrogel after the electrode is applied to the skin, because the hydrogel can adsorb a substantial amount of water before it loses its surface tack. Conversely, because it is 65+% water, it does not create chemical bonds with the skin and hair which results in pain and/or skin damage when an electrode employing a conventional adhesive-based skin interfacing member is removed after use.

To test for skin adhesiveness, samples of the hydrogel with backing removed from one side were applied to the skin and left on. This was done both with the scrim-containing hydrogel films alone and with a scrim-containing hydrogel film attached to a support backing bearing a metal conductive snap electrical terminal. How well the hydrogel adhered to the skin was observed and how easily the electrode material could be separated from the skin was noted, along with whether or not any residue was left on the skin.

The adhesiveness of the conductive hydrogel sheet or films can be quantified by the "Tack Rolling Ball Method" (TRBM) as specified by the Pressure Sensitive Tape Council, was measured. This test method for adhesive materials is detailed in the American Society for Testing Materials, Designation D3121-73 (Re-approved 1979) which test method is under the jurisdiction of ASTM Committee D-14 on Adhesives. The test utilizes an inclined trough which can be obtained through the Pressure Sensitive Tape Council, 1201 Waakegan Road, Glenview, IL 60025, that is equipped with a release lever at the top through which a 11 mm diameter steel ball is released onto the trough. The ball gains momentum as it descends the incline and rolls onto the adhesive surface whose adhesiveness is being measured, the shorter distance the ball travels thereon, the higher the adhesion value.

The test is performed as follows: Remove the backing materials from both sides of a hydrogel sample cut one inch wide and at least three inches long. The test is run in a controlled environment (72° F.±5° F. and 50% relative humidity). A hard, horizontal surface of sufficient size to conduct the test is selected. Both metal and glass plates have proved satisfactory. Before testing each adhesive sheet, clean the inclined trough thoroughly with isopropanol.

The specimen to be tested is placed flat, adhesive side up, in line with the inclined trough. The end of the specimen opposite the incline is held to the table. Only one test is run on each specimen. Each time before the ball is rolled onto the hydrogel, it is thoroughly cleaned with isopropanol, which removes any residue that might otherwise remain from a previous test, and then wiped with a lint-free, bleached, absorbent material to remove any remaining residue. After cleaning the ball or raceway is not touched. Use clean, dry tongs to place the ball on the upper side of the release. Release the ball and it will roll to a stop on the adhesive material. Measure the distance from the point where the ball initially contacts the adhesive to where the ball stops. The average of the stopping distance measurements of five or more tests is recorded. Pertinent additional comments based on visual inspection such as noticeable residue on ball, lift or adhesive from substrate, etc., are noted.

In this test, the hydrophilic gels employed in the electrodes of this invention have tack rolling ball distances of less than about 10 mm. The preferred gels have distances of less than about 5 mm. In the same test, commercial medical electrodes sold by the Minnesota Mining and Manufacturing Company ("Littmann® Brand, DEFIB-PADS") according to U.S. Pat. No. 3,998,215 give Tack Rolling Ball Distances of greater than 90 mm.

Another test to measure relative strength and stickiness of an adhesive bond is the Adhesion Energy Density Determination test. This test measures how well a hydrogel sheet adheres to a flat surface. The adhesion energy which is measured is the combined strength of the surface bond of hydrogel sheet to the flat surface and the strength of the hydrogel sheet itself.

A sample of the hydrogel sheet to be tested is placed unbacked on a clean flat stainless steel block. The block in turn is placed on a block of flexible foam which in turn is placed on a test stand. With the setup in place a steel ring is placed on top of the test sample and aligned with the test probe to be used so that the latter will descend therethrough without touching the ring. A cylindrical (1.5 inch diameter) polymethylmethacrylate test probe then descends into the sample at a constant rate to a constant depth. (In the hydrogel films tested, the descent rate was set at 0.5 mm/sec. and the penetration was set at 1.0 mm.) Before the test probe is made to descend it is cleaned with isopropanol or distilled water and dried with a lint-free cloth, to make certain no residual adhesive material is on the face of the probe before the test is begun. All tests were run at 72° F.±5° F. and at a relative humidity of 50%±5% and each test sample was stored at these conditions for at least one hour before the test. When the test probe has made its 1 mm descent into the hydrogel film and begins its return (at a rate of ascent of 0.344 cm/sec), the adhesive sample being tested has adhered to the face of the test probe. From the start of the return of the probe to complete separation of the test sample from the face of the probe, the force on the probe and the corresponding displacement is recorded using a Voland Stevens LFRA Texture Analyzer and Recorder (Voland Corporation, Hawthorne, New York). The area under the force-displacement curve is the adhesion energy. For the 1.5 inch diameter probe used, it is the adhesion energy per 11.4 cm$^2$, which is the adhesion energy density. For the work reported herein, the force was measured in grams and the displacement measured in centimeters so that all adhesion energy densities are reported in g/cm.

In this test, the hydrophilic gels of this invention display adhesion energy densities of about 2 to 30 g/cm. The preferred gels give values of greater than about 7 g/cm in this test.

The enhanced adhesive properties of the hydrogels of Examples 1 and 5, according to their Adhesion Energies and Tack Rolling Ball Distances in the above-described tests for adhesion, are evident from Table I below.

TABLE 1

| Example | Molecular Weight $\times 10^6$ | % Polymer wt % | % NaCl wt % | Irradiation Dose (Mrad) | Adhesion Energy Density (g/cm) | Tack Rolling Ball Distance (mm) |
|---|---|---|---|---|---|---|
| 1 | 4 | 4 | 5 | 0.64 | 7.7 | 15 |
| 5 | .9 | 9 | 5 | 0.50 | 15.6 | 2 |

The electrode assemblies according to this invention are suitable for application to skin in connection with both electrical signal sensing medical electrical apparatus and electrical energy transmitting medical electrical apparatus, i.e., they can be used both as sensing electrodes and as working electrodes. Examples of "sensing" electrodes are those used in electro-cardiogram (ECG), electrooculogram (EOG), electrogastrogram (EGG), surface electromyogram (EMG), electrodermal responses (EDR), electroensephalograms (EEG), visual evoked potential (VEP), and auditory evoked responses (AER). Moreover, because the hydrogels employed therein are biologically inert, the assemblies according to this invention are suited to the detection of signals requiring application to or implanted within sensitive areas of the body, such as the cornea in the electroretinograms (ERG), or in body cavities where the materials of conventional assemblies may prove unsatisfactory, such as in the summated electrocochleograms (ECOG), electro-olfactorograms (EOGs) and measuring electrovaginal potentials (EVP).

Examples of "working" electrodes for which the electrode assemblies of this invention can be used are those adapted structurally for Transcutaneous Electrical Nerve Stimulation (TENS), use as a Electro-Surgical Unit (ESU), External Cardiac Pacing (ECP) and for Defibrillation (DEFIB).

The physical, electrical and chemical characteristics of these two general types of electrodes, plus three sub-catagories of the latter type, are set forth in Table II, below.

TABLE II

| Electrode type | Size in.$^2$ | Thickness (Mils) | H$_2$O Content | Resistance ohms-cm |
|---|---|---|---|---|
| Sensing | 0.25–1.5 | 20–75 | 80–98 | 3,000-10 |
| Working | 0.5–50 | 50–115 | 80–98 | 50,000-1 |
| Defib. | 4.5–25 | " | 90–97 | 5,000-15 |
| ESU | 5.5–50 | " | 80–95 | 50,000-1 |
| ECP | 12.5–25 | " | 80–93 | 3,500-15 |

Because the PEO is cross-linked by high energy radiation, it is free of both residual monomers and chemical cross-linking agents, a very important consideration for a device which is to be affixed to the skin. If desired, the gel optionally can contain preservatives, an anti-fungal agent, a bacteriostat and the like, bearing in mind that unless special steps are taken to incorporate any such agents into the gel after it is formed, e.g., by application of a film of an aqueous solution thereof to one or both faces of the sheet of hydrophilic gel, the materials selected must be able to withstand the irradiation employed to produce the hydrophilic gel.

GENERAL CHARACTERISTICS OF HYDROGEL INTERFACING MEMBER

The following is a summary of the properties of the hydrophilic gels of this invention.

BIOCOMPATIBILITY

The hydrophilic gel is inert and is not metabolized. It has a normal pH of about 7, which is allowed to "float" between 6 and 8. They have a zero irritation index. Because it is produced by irradiation, the gel is virtually or completely sterile, with less than 10 colonies per cubic centimeter (the measurable limit).

The hydrogel contains no extraneous or other objectional ingredients. It does not contain extraneous chemicals such as monomers and cross-linking agents, which are present in chemically linked cross-linked gels, or solvents, etc., which are an integral part of formulated adhesives. All ingredients have proven bioacceptability on contact with the skin. Normal exudants flow into the matrix of the gel away from the user's skin. Its hydrophilic properties eliminate the common requirement for abrasive treatment and/or other skin preparation.

The biocompatibility of the hydrogel, i.e., its hypoallergenic properties, was tested in accordance with the method described in the Federal Hazardous Substances Act (modified somewhat in accordance with the draft protocol for Dermal Toxicity Testing for Medical Devices in Contact with Skin). An irritation index of zero was returned when tested on abraded and unabraded skin of New Zealand white rabbits.

SPECIFIC ION CONTROL

Experience has shown that specific ion control with even distribution within the conductive matrix is of paramount importance in electrode performance. The precise ion level and dispersion in the process employed to produce the hydrogel lends itself perfectly to the production of a unique family of controlled conductive-adhesive transmission components. Although the polymer matrix theoretically could hamper ion mobility, the volume resistivity of the hydrogel remain low.

HYDROPHILIC CHARACTERISTICS

The hydrogel contains no free water. The water in the hydrogel is an integral part of the gel structure and therefore cannot be separated therefrom by physical means such as pressure. Thus, the matrix remains homogeneous under gravity and even with freezing. Its imbibing property enables the hydrogel to cleanse the body surface of water soluble exudates and secretions by drawing them up into the gel by osmosis, thus lowering the skin irritation factors commonly associated with other organic polymers. The gel pad has a distinct advantage of conforming itself to the irregularities of human skin, producing a substantially uniform contact. This is an important characteristic because poor skin contact can cause electrical noise or current loss, which can change the accuracy of a biopotential recording or the efficacy of an electrical energy treatment. The high water content also precludes the necessity of preparatory skin shavings which some commercial electrodes require.

ADHESIVE PROPERTIES

The hydrogel's adhesive characteristics are a function of its ability to conform to minute irregularities on the surface on which it is placed, while retaining its cohesive properties. This characteristic meets the criteria of an adhesive, without the necessity of additional chemicals. The degree of adhesion to a given surface is a function of the degree of irregularity or porosity of the surface. The hydrogel retains its adhesive quality even while absorbing normal perspiration. The viscostatic properties of the hydrogel within the gel structure allows it to flow into the tiny interstices of the surface to which it is placed, thereby allowing intimate uniform contact between itself and that surface. This type of adhesiveness allows it to adhere to skin without employing additional chemical bonding agents, which permit the hydrogel to be removed from the skin without pain, skin damage or hair pulling and without leaving any residual components of the gel on the skin itself, as the components are permanently bound within the gel structure. A further discussion of the adhesive properties of the hydrogels is found in the concurrently filed application identified hereinabove.

ELECTRICAL CHARACTERISTICS

The starting materials used to produce the hydrogel can be formulated with a wide range of amounts and types of ionic materials to produce hydrogels having predictable electrical characteristics. The uniform distribution of selected ions results in correspondingly reproduceable electrical properties throughout the hydrogel, thereby lending itself to a wide variety of applications based on its conductive and capacitive properties. Furthermore, the predictable volume resistivity of the hydrogel lends itself to many critical medical applications.

Electrolytes that can be used in the hydrogel include most cations, e.g., ammonium, sodium, potassium, lithium, magnesium, calcium, etc., and both simple and complex anions, e.g., chloride, sulfate, carbonates, nitrates, and anions of organic acids, e.g., acetic, citric, adipic, tartaric, lactic, propionic, glutaric and maleic acids, the latter being preferred in electrodes where corrosion of the metallic connector may be a problem. Magnesium acetate is especially suitable in this respect. The volume resistivity remains constant throughout the gels intended use, allowing virtually zero decay in the resistance of the skin in medical applications, while allowing an upward even flow of skin excretions through the matrix away from the user. This change is uniform throughout the cross sectional area of the gel because of its balanced osmotic hydrophylic properties.

PHYSICAL PROPERTIES

The basic sheet form of the hydrogel has both structural integrity along with resilient memory which permits it to return to and retain its original form when pressure is applied to the X-Y or Z axis. The product will withstand loss of water with a force of about 20 psi on a single surface, unlike other types of gels which exude water under the influence of gravity. Its high specific heat is another useful property. The hydrogel sheet is structurally unchanged and functional over a wide range of temperatures beyond its use range. The amount of energy required to raise the temperature of the sheet adds a safety margin in many medical applications. It can also be useful in some combination therapy applications involving heat/cold and electrical stimulation.

Because the hydrogel sheet or film is produced with high energy radiation, such as that produced by an electron accelerator, as produced it is sterile.

Particular advantages realized with electrodes employing the hydrogel are its stable electrical properties and its excellent adhesion to the skin. A superior medical electrode should not store electrical charge, should have a low solution potential with the skin and should be of low impedance. The hydrogels employed in the electrodes of this invention have all of these characteristics. The electrodes also adhere firmly to the skin, ordinarily without the necessity of external adhesive support, depending upon the duration of the application. Also, the surfaces of the hydrogel which are exposed to air during use slowly form a dry crust over a period of time, thereby preventing the bulk of the hydrogel film from drying out and acquiring altered electrical conductivity properties. This is particularly useful for long term applications.

The electrodes of this invention also exhibit further superior properties upon removal after use. Although the electrodes readily adhere to the skin, they can very easily be removed therefrom in a painless manner without damaging the skin, as do conventional commercial adhesive products. Moreover, upon removal, the electrode leaves no visible residue on the skin, as do many liquid gel-based electrodes. In fact, liquid gel electrode materials must be wiped off the skin in a relatively painstaking manner, frequently by application of soap and water. During application, the hydrogel of the electrodes of this invention does not stain or stick to clothing. All of these advantages are accomplished employing ingredients which have an excellent history of biocompatibility so there is little likelihood of skin eruption or irritation.

Both sensing (detecting electrical signals on the skin) and working (transmitting electrical energy to the skin) electrodes according to this invention have numerous advantages over the prior art versions presently available commercially. Some of these are listed in Table III below.

TABLE III

| Property | | Advantage |
|---|---|---|
| 1. Thermal | Working: | Less chance of burns in ESU use. |
| | Sensing: | Less temp. drift in ECG/EEG use. |
| | Both: | Patient friendly; can be warmed to skin temp.; wide range of storage conditions acceptable. |
| 2. Adhesion | Working: | Less chance of radio freq. burns; better contact due to detachment in ESU use; adheres to paddle, no chance of a short due to movement in DEFIB. |
| | Sensing: | Less motion artifact in ECG/etc. Less false alarms due to detachment. |
| | Both: | No tapes, foams needed. |
| 3. Clarity | Working: | Able to see burns thru ESU, TENS & DEFIB applications. |
| | Sensing: | Can detect local skin reactions. |
| | Both: | User preference, clean look. |
| 4. Impedance | Working: | Able to select medium impedance (by control of salt content) for EGU & DEFIB uses. |
| | Sensing: | Able to select low impedance for ECG/EEG/EMG/etc. applications. |
| 5. Uniform Impedance | Working: | No rf burns due to hot spots in ESU applications. No patient burns due to arcs in |

TABLE III-continued

| Property | | Advantage |
|---|---|---|
| | | DEFIB applications. |
| | Sensing: | Low DC offset due to un-matched ECG electrodes. |
| | | True signal reproduction in relative EEG/EMG signals. |
| 6. Skin Contact | Working: | Uniform application of power thru skin in DEFIB, ESU, ETC. |
| | Sensing: | Less noise in ECG/EEG use. |
| | Both: | Low surface impedance. |
| 7. Self-Sealing | Working: | Less edge effect in ESU use. No shorts due to product migration in DEFIB use. |
| | Sensing: | Low external pressure induced DC offset in ECG/EMG use. |
| | Both: | Can be cut to size. Less water loss in long term use. |
| 8. Conformability | Working: | Less burns at thin, boney sites in ESU use. Less arcs at hairy, thin, boney sites in DEFIB use. Less Air Gaps. |
| | Sensing: | Low motion induced artifact. Stays in place in ECG use. |
| 9. Bioburden | Both: | Very Low. |
| 10. Reuseability | Both: | Can be easily rehydrated a number of times by moistening with water. |

PREPARATION OF HYDROPHILIC GEL

A hydrogel conductive sheet suitable for use in a medical electrode of this invention can be produced by mixing the water soluble linear polyethylene oxide with the selected electrolyte and water to form a viscous feed. A convenient procedure is to gradually blend the dry polymer into an aqueous solution of the electrolyte, either at ambient or elevated temperatures. Alternatively, a hot solution of the polymer can be prepared and a concentrated solution of the selected salt slowly blended therewith to achieve the desired or final concentration of electrolyte and polymer. The viscous liquid feed is then applied to a flat surface to form a liquid film thereon, e.g., a film of polyethylene or a polyethylene coated sheet of paper. To contribute to the strength of the hydrogel both in tension and flexure a low area-weight scrim can be incorporated during fabrication before cross-linking. The scrim can be of mesh type geometry, either woven or non-woven, e.g., non-woven monofilaments heat sealed together at their interstices or a sheet of thermoplastic polymer with holes in a geometric pattern heat-stamped therein, provided the scrim in is of substantial open area and low area weight, e.g., from about 0.1 to 5 mil in thickness and an area weight of about 0.002 to 0.2, preferably about 0.003 to 0.1 g/inch$^2$. The scrim is preferably fabricated from a natural or synthetic hydrophobic polymer, e.g., a polyethylene, polypropylene, polyester, polyamide homopolymer. These polymeric materials are preferably non-plasticized so that they cannot leak impurities into the hydrogel.

The resulting liquid film is then subjected to high energy radiation such as an electron beam, where it is converted into a solid gel. To facilitate production, the liquid film is preferably backed on one or both sides with a thin peelable hydrophilic sheet, e.g., polyethylene or plastic coated release paper, before it is irradiated. Either or both plastic sheets are then peelably removable after formation of the hydrogel sheet, either before packaging or before use. The hydrogel sheet, which is now a viscoelastic solid, can be cut to desired size and shape for use as the conductive element that contacts the skin in a fabricated electrode device. Depending upon the application, different types of backing sheets can be used on one or both sides of the hydrogel sheet, e.g., a non-peelable sheet can be used on one side only or a peelable sheet on one side and a non-peelable sheet on the other.

The polyethylene oxide formulations useful in these applications include those incorporating and binding high concentrations of water while maintaining adequate surface tack (adhesiveness) and sufficient strength (cohesiveness). The starting water soluble linear polyethylene oxide must have a molecular weight high enough to readily cross-link and form a viscous solution for processing. As stated above, generally polymers with weight average molecular weights from about $0.05-10\times10^6$, preferably about $0.26-6\times10^6$, e.g., $0.54-4\times10^6$ Daltons are employed. Typically an aqueous solution of about 0.1 to 15 wt%, preferably about 0.7 to 10 wt% of a water soluble salt, preferably a dermatologically acceptable metal salt, more preferably an alkali metal salt, e.g., sodium or potassium chloride is employed, the specific concentration depending on the conductivity desired in the hydrogel produced therefrom generally transverse conductives of less than 1,000 (ohm-cm)$^{-1}$ and preferably less than 100 (ohm-cm)$^{-1}$ are desired. Such a salt solution is combined with a water soluble linear polyethylene oxide by mixing to produce a homogeneous viscous solution. The concentration of polymer therein typically is from about 2 to 35 wt%, preferably about 4 to 25 wt%, e.g., 7 to 10 wt%, of the overall solution, depending upon its molecular weight and the salt concentration therein, i.e., high molecular weight PEO polymers are less soluble in high concentration salt solutions than lower molecular weight PEO polymers. The polymer-salt-water solution should be viscous enough to form into a sheet-like configuration, e.g., a liquid film of about 0.1 to 2 mm thickness, before cross-linking. Illustration viscosities range from about 2,000 to 2,000,000 cps. The polymer-salt solution is formed into a liquid sheet or film by coating onto a backing film or sheet. If a scrim is incorporated into the body of the solution, the solution should project beyond both faces of the scrim and all surfaces of the scrim should be wet with the solution. This casting technique can be continuous, thereby forming an elongate continuous sheet or film, or discontinuous, i.e., applying individual pools of the solution of a size and shape corresponding to single electrodes. Any quantity of the viscous solution may be applied to a backing film to form a sheet of hydrophilic gel capable of yielding a plurality of individual interfacing means for individual electrodes, or a large single sheet which can be cut up to form a plurality of interfacing means or the sheet can be cut into long strips and rolled into rolls as a tape. The thickness of the aqueous PEO-salt solution that is applied to the backing sheet generally is dictated by the viscosity of the solution and whether or not a scrim is incorporated therein.

After the viscous solution is applied or cast to the desired thickness, it is then subjected to cross-linking high energy irradiation, such as a high energy electron flux as produced by an electron accelerator or Van De Graaf generator. If conditions are selected which exclude atmospheric oxygen are taken, even gamma radiation may be used. The major requirement is that the beam of electrons be of sufficient energy to complete penetrate the solution, so that the solution receives a radiation dose effective to cross-link the entire cross section of the sample. Proper dose/energy/thickness relationships are readily available to those skilled in the art of radiation processing and therefore need not be discussed in detail. To achieve the desired degree of uniform cross-linking, i.e., effective to convert the viscous polymer-salt-water solution into a viscoelastic solid gel, doses typically of about 0.25 Mrads to 5.0 and usually about 0.35–1.5 Mrads are required, depending upon the selected polymer, its concentration, the selected salt and its concentration and the presence or absence of selected functional or therapeutic agents.

Generally speaking, higher polymer concentrations require higher irradiation doses to produce an acceptable viscoelastic solid gel than lower polymer concentrations.

After the conductive hydrogel sheet is irradiated and converted into a viscoelastic solid, it can then be incorporated into an electrode. First it is cut to size, if it is not formed in its desired final shape. If both faces of the hydrogel are covered with backing material, one of its faces is freed from the backing material. The side freed from the backing material is then affixed to a non-porous support conductive member, e.g., a material which contains a conductive metal button or snap which is capable of receiving an electrode lead wire and connector to an external electrical apparatus. The electrode is then ready to be sterile packaged. The package preferably is a gas, moisture and microorganism impermeable sealed pouch or envelope, e.g., formed by heat sealing a heat sealable aluminum foil polymer laminate.

When packaged electrode is ready for use, it is removed from its package, the remaining backing material is released by peeling it from the gel interfacing sheet, and it is applied to the skin of the patient. The electrode lead wire is then attached to the electrode at the fastener conductive member. Alternatively, the lead wire can be attached to the electrode before the remaining backing material is removed, the backing material then removed and the electrode with the connecting wire attached applied to the skin. Alternatively, the packaged electrode can be provided with its own electrode lead wire already attached. The same sequence of backing material removal and application of the electrode to the skin would then apply without the necessity of attaching a lead wire to the electrode before or during application.

The hydrogel interfacing member of the electrodes of this invention have high adhesive strengths, which means that they can readily be affixed to the skin and will adhere thereto with little risk of accidentally dropping off through loss of adhesion. Because the interfacing member is water based, it is relatively immune to the effects of moisture on the skin and will not release as a result of perspiration forming under the electrode while affixed to the skin. They also have high cohesive strengths, which means that they can be removed from the skin after use without leaving any visible residue. Interestingly, although the gels have a high adhesive strength, it is not high enough to pull hairs from the skin or irritate the skin when the gel is removed therefrom.

The medical electrodes of this invention containing a sheet of a PEO hydrophilic solid gel as disclosed herein as a skin interfacing member can assume a wide variety of shapes and construction, e.g., not only those available commercially today which employ a semi-solid or solid gel, those other disclosed in the prior patents cited herein above as being directed to a medical electrode, whose disclosures are incorporated herein by reference.

Because the PEO hydrogel will lose water under ambient conditions, it must be stored in a water and gas impermeable container, e.g., a polyfoil packet formed from the laminated plastic conventionally used to store measured amounts of freeze-dried or ground coffee. A thus-packaged electrode according to this invention will be sold under the trademark "Stratum" by Alternative Design Systems, Inc. Sealed envelopes are conventionally produced by heat sealing a pair of sheets of thin plastic around the hydrogel sheet-backing sheets laminate, or medical electrode in which a hydrogel sheet is mounted, or by heat sealing the open end of an otherwise sealed packet or envelope formed from a single sheet of the laminate and which contains a hydrogel laminate or a medical electrode comprising it.

If the film or sheet of PEO hydrogel is to be stored separate from the components of the medical electrode with which it is to be used, both faces thereof are preferably covered with a sheet of peelable release liner, e.g., polyethylene or polyethylene coated paper. If the sheet of hydrogel is to be stored mounted in the medical electrode with which it is to be used, its exposed face, i.e., the face to be applied to the skin, is covered with such a release liner. If both faces are covered with a release liner, optionally different liners can be employed, one of which is more readily removable therefrom than the other, e.g., a sheet of polyethylene covering one face and a sheet of "Mylar" plastic covering the other, thereby ensuring that a predetermined face of the film or sheet is exposed first. In some end use applications, one of the faces of the film or sheet is covered with a conductive liner which is not removable and is used as a conductive member in the final electrode assembly.

The PEO hydrogel sheet or film can be packaged singly or in multiples between the release liner or liners. In TENS end uses, it is desirable to mount a plurality of spaced apart circles, squares or rectangles of the film or sheet of the hydrogel on a plastic sheet, e.g., a 2 mil film of "Mylar" plastic and cover their exposed face with a different release liner, e.g., a 2 mil film of polyethylene or a sheet of polyethylene coated paper release liner. Either or both of the facing films can be appropriately scored to facilitate removal of the units of PEO hydrogel sequentially. If desired, one face of a plurality of units of the hydrogel can be covered with a large backing sheet, one facing film which is unscored and the other face covered with a release liner of the same dimensions as the units of the hydrogel so that a unit of the hydrogel and the latter release liner can be peeled off together, one at a time from the large backing sheet.

In another embodiment, a large sheet of a laminate formed from the PEO hydrogel and films of plastic covering its faces, e.g., a film of polyethylene on one face and a film of Mylar on the other, is scored at spaced intervals in both directions thereby producing a plurality of severable square or rectangular units of the laminate, each for use individually in conjunction with a medical electrode by tearing the laminate along a pair of perpendicularly positioned lines, thereby releasing a unit of the laminate from the sheet.

When the sheet of PEO hydrogel is of the same dimension as a release liner covering an exposed face thereof, removal of the latter is facilitated if the latter is slit into pieces, thus providing an edge which can be easily raised with a fingernail or tool.

If desired, a plurality of circles, squares or rectangles of the hydrogel with a release liner covering one face can be "stacked" one upon the other so that a column of such units of the hydrogel sheet with both faces covered with a release liner is formed. Desirably, in such an arrangement, one side of the release liner has a higher adhesive value than the other, so that only one unit of the hydrogel is removed at a time from the column. Such columns can be conveniently stored in glass jars or aluminum lined paper tube with a moisture impervious cap which form a gas and moisture impervious sealed container.

The following is a descriptin of specific end use applications of the ionic PEO hydrophilic sticky surfaced viscoelastic solid gels employed in the medical electrodes of this invention and the advantages associated therewith.

TENS

The TENS (Transcutaneous Electrical Nerve Stimulation) electrode coupling media is produced from low to medium ionic concentration, e.g., about 4 to 5 wt% of sodium chloride, hydrogel sheets. It is used as a disposable interface between a "standard" reuseable carbon electrode and the skin. The substance can also be used as an electrolyte in contact with its own carbon electrode material. The floating pH of the hydrogel is especially important since characteristics change under long term high current flow. The inert ingredients preclude skin irritation and the osmotic properties permits exudant to be carried away. The uniform ion control allows uniform current distribution and the hydrophilic properties prevents any air-gaps that can cause alternating current rectification. The excellent adhesive characteristics prevent accidental electrode detachment and the consistent electrical properties assures continuous effective treatment. The cohesive properties allows the hydrogel sheet to be cut to size and easily removed from the skin and electrode, offering true ease of use. This also holds true of the totally disposable product where ease of use and no clean-up are controlling factors. Finally the high specific heat and intimate contact becomes a deterrent to "hot spots" and any thermal burn potentials.

ESU

The ESU (Electro-Surgical Unit) electrode is produced from low ionic hydrogel sheet, e.g., 3.5 wt% NaCl. The dispersive radio frequency (grounding pad) return electrode application is a perfect conductive/adhesive application. The adhesive safety factor which prevents electrode removal and subsequent RF burns is of paramount importance. The precise ionic distribution and control prevents current pooling and small thermal burns. The hydrophilic properties lessen interference from surgical fluids and assures close physical contact, thereby preventing muscle stimulation from rectified current. The high specific heat provides another safety factor in diminishing edge effect heating and electrolyte drying. The hydrogel has inherently uniform solids distribution and is a thermodynamically homogeneous system, which precludes uneven gel distribution during storage (gel migration) and thus ensures adequate surface area for proper current dispersion from the body. The biological inertness of the hydrogel assures that local skin reactions, which could be confused with possible RF burn, will not be produced. The hydrogel's chemical inertness assures no ingredient breakdown via electrolysis and the hydrogel's excellent response to elevated temperatures also assures performance under adverse use conditions.

EKG (ECG)

The PEO hydrogel-based EKG (electrocardiogram) electrodes have the widest variety of specific use applications, made possible by the ability to produce hydrogels of specific ionic strength. The ion concentration is chosen from a high, e.g., 7-8 wt% sodium chloride, percentage for high performance exercise use to low, e.g., 5-6 wt% sodium chloride, concentrations for long term applications. The ability to use ions that have previously been hard to control allows the production of a near perfect electrode on a consistent basis. The unique ability of the hydrogel to be compressed without any associated signal drift makes it ideal for clinical situations. The bound PEO matrix provides a stable signal sensing electrolyte for consistent recording, regardless of changing skin or temperature conditions. The excellent adhesive properties of the hydrogel provides added safeguards against "lead-loss" alarm conditions and the cohesive component provides the sought after ease of use quality. The excellent skin friendliness makes it a perfect choice for long term contact with the added safety of a floating pH. The hydrophilic characteristics allows good conduction without the patient discomfort of skin abrasives or shaving. Finally, the excellent response to extreme temperatures makes EKG electrodes based on the PEO hydrogels of this invention a good choice for emergency field applications.

DEFIBRILLATION

The Defibrillator pad is produced from a sheet of medium ion percentage, PEO gel, e.g., about 8 wt% NaCl. The pad is usually used as a conductive media for the application of large amounts of electricity (voltage and current) and also used as a sensing electrolyte for EKG monitoring thru the same electrodes. The excellent electrical properties allows efficient delivery of the therapeutic charge of electricity without a loss of monitoring capability due to its low DC offset. The bound PEO matrix prevents the product from pooling during storage and the unique thermal properties of the gel makes it the perfect choice for field use of these devices. The adhesive component assures proper paddle contact without the fear of electrode cream running, which allows repeated re-positioning or re-application of the paddles while maintaining effective skin contact. The hydrophilic properties of the gel sheet assure uniform skin contact without "pitting" and also eliminates the necessity of any skin preparation. The structural stability of the gel sheet allows greater user pressure upon paddle application without fear of pushing the gel away from the contact area. Finally, the clear glass-like property of the gel sheet allows full view of any trauma related injuries.

BIO-FEEDBACK

The Bio-Feedback electrode is produced from a high concentration ionic gel sheet, e.g., 7-8 wt% NaCl. Advantageous characteristics of the hydrogel sheet are its ability to firmly adhere to the patient's skin because of it adhesiveness and its ability to be re-positioned because of the cohesiveness. Its specific even ionic concentration allows it to be used with a wide variety of home and clinical electrodes, and permits immediate signal reception. The hydrophilic properties of the gel sheet allow many possible placement sites without the need for any skin preparation. The bio-compatibility and skin friendliness makes long term use possible. The qualities of this product also find identical applications in the EEG, EMG, ENG and Evoked Potential fields. Specific electrical qualities necessary in all the above uses involve low noise potential and small DC offsets because of the low level signals involved. The gels bioinertness is especially important since these applications are frequently proximate to the eyes and mouth.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views, and wherein.

Figure 1:
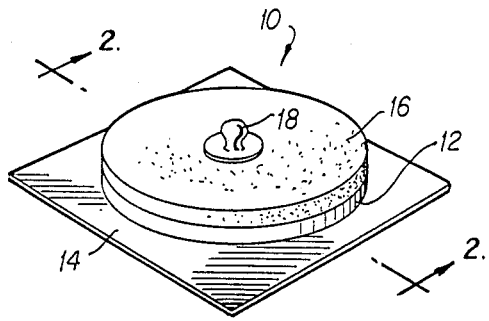
FIG. 1 is a perspective overhead view of a TENS electrode embodying the principles of this invention.
Figure 2:
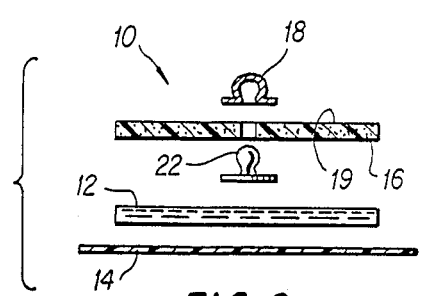
FIG. 2 is an exploded cross-sectional view of the components of the TENS electrode of FIG. 1, along line 2—2.

Referring now more particularly to the drawings, there is shown in FIGS. 1 and 2 a TENS electrode assembly, indicated generally as 10 having a hydrogel 12 of this invention mounted between a release liner 14, e.g., a 2 mil metallized Mylar, and a polyurethane foam pad 16. Electrical connection between the hydrogel 12 and a stainless steel or silver-silver chloride coated snap electrical connector 18 mounted on the exposed face 19 of pad 16 is achieved by a carbon coated eyelet 22 which is forced through pad 16 and into permanent seated arrangement with the interior of connector 18.

Figure 3:
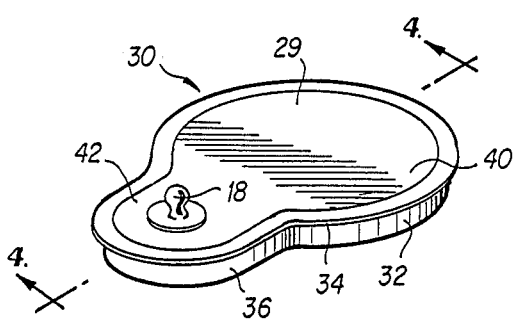
FIG. 3 is an alternative TENS electrode assembly of this invention.
Figure 4:
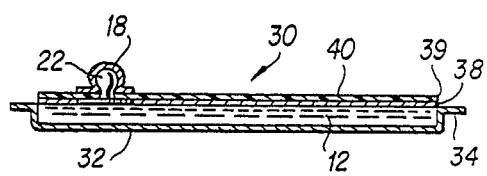
FIG. 4 is a cross-sectional view taken along line 4—4 of FIG. 3.

FIGS. 3 and 4 show an alternative embodiment of a TENS electrode assembly indicated generally as 30 in which the electrode is mounted for storage in a gas impermeable thermoformed plastic tray 32, e.g., metallized Mylar or polystyrene, having a lip 34 around its entire upper periphery and an elongate neck portion 36 adapted to receive a correspondingly shaped neck portion 42 portion of the electrode 30 bearing a snap connector 18 and associated mounting eyelet 22. The upper face of the hydrogel 12 portion of the electrode 30 is covered by a conductive plastic film 38, e.g., 5 mil carbon coated PVC, which in turn is covered by an insulating plastic film 39, e.g., 5 mil PVC. Electrical connection between hydrogel 12 and snap connector 18 is achieved by forcing eyelet 22 through insulating film 39 into seated arrangement in the interior of connector 18, whose base is mounted on the upper face 40 of insulating film 39, and contacting the base of eyelet 22 with the upper face of hydrogel 12. For storage purposes, tray 32 can be rendered gas and moisture impermeable by heat sealing a film of plastic (not shown), e.g., metallized Mylar, around the complete periphery of 32 at lip 34.

Figure 5:
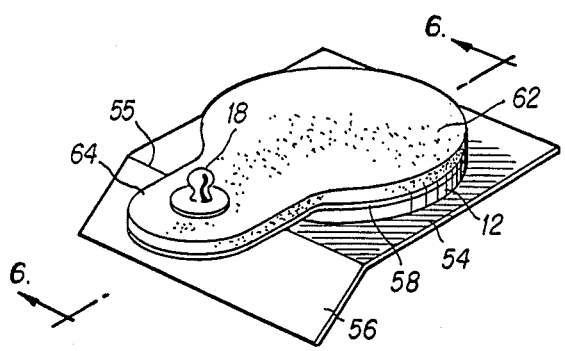
FIG. 5 is still another TENS electrode is in accordance with this invention.
Figure 6:
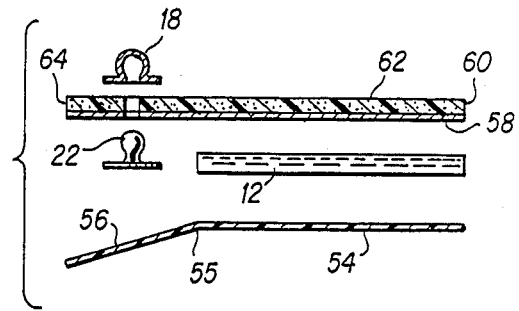
FIG. 6 is an exploded cross-sectional view of the components of the TENS electrode of FIG. 5, taken along line 6—6.

In the electrode assembly of FIGS. 5 and 6, the hydrogel 12 is mounted on a rigid release liner 54 and its upper face is covered by a carbonized conductive PVC film 58, which in turn is covered by an insulating pad of polyurethane foam 62. The conductive film 58 and insulating pad 58 have a neck portion 64 which extends beyond hydrogel 12 and on which is mounted a snap connector 18 by eyelet 22, in a manner comparable to the electrode of FIGS. 1-4. The release liner 54 also has a portion 56 which extends beyond hydrogel 12 and downwardly therefrom by virtue of a thermoformed bend at line 55 thereof to facilitate mounting an electrical wire connected to the medical apparatus to snap connector 18 prior to removing release liner 54.

Figure 7:
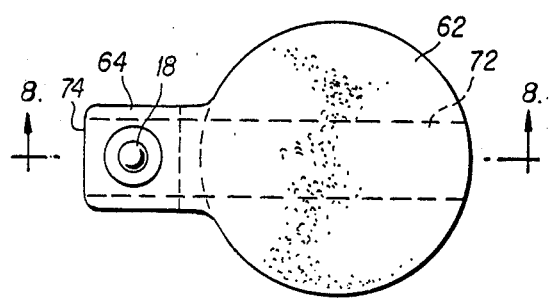
FIG. 7 is a perspective overhead view of an EKG electrode according to this invention.
Figure 8:
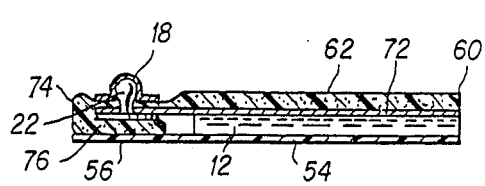
FIG. 8 is a cross-sectional view of the electrode of FIG. 7, taken along line 7—7.

The construction of the electrode of FIGS. 7 and 8 is similar to that of the electrode of FIGS. 5 and 6, except that the member for providing electrical connection between the base of eyelet 22, mounted on the exposed face of foam pad 60, and hydrogel 12 is a metallized conductive strip 72 adhesively affixed to the bottom face of foam pad 60, through which eyelet 22 projects as well as through conductive strip 72 so as to provide electrical connection with eyelet 22. Also, the base of eyelet 22 is protected from contact with hydrogel 12 by an extension 74, 76 on the neck portion 64 of pad 62 which is folded around the end and under face of that neck portion, respectively, and affixed adhesively to the under face thereof. In this embodiment also, the release liner 54 extends beyond hydrogel 12 to facilitate its removal prior to use.

Figure 9:
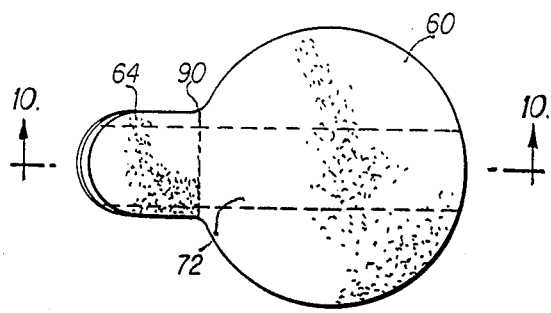
FIG. 9 is a perspective overhead view of an alternative EKG electrode according to this invention.
Figure 10:
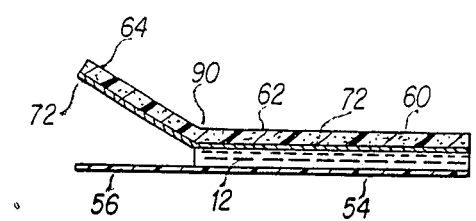
FIG. 10 is a cross-section view of the electrode of FIG. 9, taken along line 10—10.

The embodiment shown in FIGS. 9 and 10 consists solely of hydrogel 12, release liner 54, the same conductive metal strip 72 as in the embodiment shown in FIGS. 8 and 9 and the foam pad 60. Instead of a connecting eyelet 22, the neck portion 64 of pad 60 projects upwardly away from the correspondingly positioned neck portion 56 of release liner 54 by a thermoformed bend at line 90, to facilitate attachment of an alligator clip thereto and to reduce the likelihood of the exposed portion of metal strip 72 contacting the patient's skin.

Figure 11:
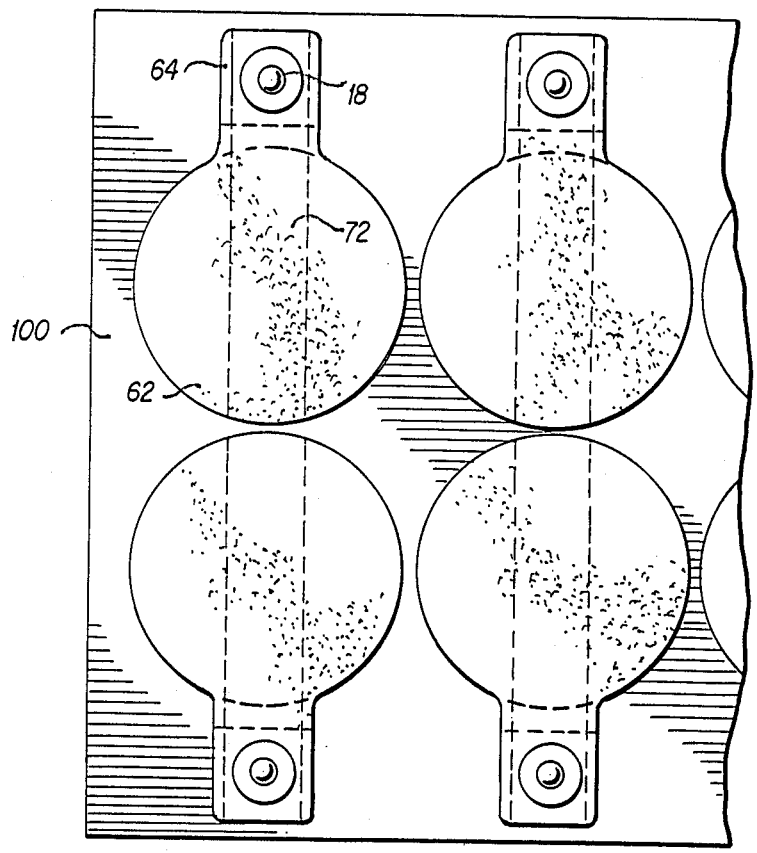
FIG. 11 is a fragmentary top elevation view of a backing sheet bearing four of the EKG electrodes of FIGS. 7 and 8.

The embodiment of FIGS. 11 and 12 illustrates how a plurality of electrodes otherwise identical in construction to the embodiments shown in FIGS. 7 and 8 can be mounted on a common release liner 100.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight, unless otherwise indicated.

EXAMPLE 1

A liquid film (ca. 50 mil) of a solution of 4 wt% polyethylene oxide (approximate weight average molecular weight $4 \times 10^6$) and 5 wt% sodium chloride in water is cast onto a 1 mil film of polyethylene backing material. A polyethylene non-woven scrim (0.016 grams/inch$^2$) area weight is immersed into the viscous solution near its center. The scrim-containing solution is covered with a second sheet of 1 mil polyethylene film backing material, producing a sandwich 52 mil thick. This sandwich is then passed across the beam of a Van De Graaf generator, where it receives 0.64 Mrads of irradiation. The liquid PEO film is thus converted to a film of a solid viscoelastic hydrogel. A one inch square sheet is cut from the sandwich and the backing materials on both sides of the sheet are removed. The sheet of scrim-containing solid hydrogel is affixed to the back side of a conductive silver/silver chloride snap, the front of which is embedded in a sheet of adhesive polyurethane foam with the top of the snap protruding therefrom. This configuration of conductive hydrogel, silver/silver chloride button and polyurethane foam, constitutes a test electrode unit. Two identical such electrode units are then joined together hydrogel back to hydrogel back to form an electrode pair. This electrode pair is then tested to determine its electrical responses for use as a medical electrode according to the proposed standards for pregelled ECG disposable electrodes by The Association for the Advancement of Medical Instrumentation (*Standard For Pregelled ECG Disposable Electrodes*, Association for the Advancement of Medical Instrumentation, February 1984 Revision). The guideline values specified by The Association for such electrode pairs in the following electrical measurements are:

| Electrical Characteristic | Standard Values |
|---|---|
| (a) Initial offset voltage V(0)(mV) | <100 |
| (b) Impedance at 60 Hz Z(60)(Ohm) | <3000 |
| Other important electrical characteristics which yield superior electrodes: | |
| (c) Initial resting offset voltage V(IO)(mV) | — |
| (d) Ten second offset voltage V(10)(mV) | <100 |
| (e) Offset voltage after short V(S)(mV) | <100 |

The values obtained for the electrode pair of Example 1 were:

| V(IO) | V(0) | V(10) | V(S) | Z(60) |
|---|---|---|---|---|
| 0.9 mV | 13.8 mV | 10.8 mV | 4.7 mV | 22.7 Ohm |

EXAMPLE 2

The hydrogel of this example is identical to that of Example 1, except 5 wt% of potassium chloride was used to provide the ions to render the hydrogel sheet conductive. The conductive values obtained for the electrode pair described in Example 1 in the above-described tests were:

| V(IO) | V(0) | V(10) | V(S) | Z(60) |
|---|---|---|---|---|
| 1 mV | 11.0 mV | 8.2 mV | <100 mV | 24.7 Ohm |

EXAMPLE 3

The hydrogel of this example is identical to Example 2, except 0.5 wt% potassium chloride was used to provide the ions to render the hydrogel sheet conductive. The electrode-pair gave the following values in the above-described tests:

| V(IO) | V(0) | V(10) | V(S) | Z(60) |
|---|---|---|---|---|
| <1 mV | 12.5 mV | 10.2 mV | <100 mV | 74.3 Ohm |

EXAMPLE 4

The hydrogel of this example is identical to Example 3 except 10 wt% potassium chloride was used to provide the ions to render the hydrogel sheet conductive. The electrode-pair gave the following values in the above-described tests:

| V(IO) | V(0) | V(10) | Z(10) | Z(60) |
|---|---|---|---|---|
| <1 mV | 8.8 mV | 6.2 mV | <100 mV | 18.0 Ohm |

EXAMPLE 5

The hydrogel of this example is identical to Example 1, except the PEO polymer used had a weight average molecular weight of $0.9 \times 10^6$ and it was used at a concentration level of 9 wt%. The electrode-pair gave the following values in the above-described tests:

| V(IO) | V(0) | V(10) | V(S) | Z(10) | Z(60) |
|---|---|---|---|---|---|
| .25 mV | 15.5 mV | 9.8 mV | 5.4 mV | 45 Ohm | 28.8 Ohm |

EXAMPLE 6

The hydrogel of this example is identical to Example 1, except the polymer used is polyvinyl pyrrolidine of weight average molecular weight of $0.36 \times 10^6$ and it was used at a concentration level of 15 w%. The electrode-pair gave the following values in the above described tests:

| V(IO) | V(0) | V(10) | V(S) | Z(10) | Z(60) |
|---|---|---|---|---|---|
| 9.2 mV | 19.6 mV | 13.4 mV | 10.1 mV | 36.6 ohm | 24.8 ohm |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a medical electrode adapted for providing electrical contact with a patient's skin and comprising:
   (a) a conductive member including means for connecting the medical electrode to an external electrical apparatus; and
   (b) interfacing means comprising a solid sheet of a conductive viscoelastic hydrophilic gel, connected electrically with the conductive member, having a face adapted for interfacing electrically with and adhesively to the patient's skin, which sheet is more cohesive than it is adhesive to the patient's skin and is mechanically connected more firmly to the conductive member than it can be adhesively affixed to the patient's skin, thereby enabling concurrent removal of the conductive member and the sheet from the skin after use without leaving a noticeable residue on the skin, the improvement wherein the hydrophilic gel is a homogeneous aqueous mixture, substantially free of unbound water, monomers and cross-linking agents, consisting essentially of (i) water;

(ii) an amount dissolved in the water of a water soluble magnesium or calcium salt effective to reduce the transverse electrical resistance of the sheet to an impedance at 60 Hz of less than 1,000 ohms, and (iii) an amount dispersed uniformly throughout the water of from about 2 to 35 wt% of a cross-linked polyethylene oxide, effective to form with the water a tacky surfaced viscoelastic solid, which hydrophilic gel is produced by subjecting a liquid film of an aqueous solution, having a viscosity of about $2-2,000 \times 10^3$ cps, of the electrolyte and a linear water soluble polyethylene oxide having a weight average molecular weight from about $0.05-10 \times 10^6$ Daltons to an amount of high energy radiation effective to convert the liquid film to a sheet of the viscoelastic solid having an adhesive face which in the rolling ball tack test gives a rolling ball distance of less than about 10 mm and an adhesion energy force in the Adhesion Energy Density Determination Test of about 2 to 80 g-cm/cm$^2$ which adhesive sheets have greater cohesive strength than adhesive strength, whereby the sheet can be removed from a surface to which it is affixed without leaving a visible residue.

2. An electrode according to claim 1, wherein the hydrophilic gel contains immersed therein a low area-weight scrim.

3. An electrode according to claim 2, wherein the scrim is a sheet of non-woven polyethylene.

4. An electrode according to claim 1, wherein the water soluble salt is present in a concentration of about 0.1 to 15 wt%.

5. An electrode according to claim 4, wherein the water soluble salt is magnesium acetate.

6. An electrode according to claim 1, wherein the concentration of the polyethylene oxide in the hydrophilic gel is about 4 to 25 wt%.

7. An electrode according to claim 1, wherein the concentration of the polyethylene oxide in the hydrophilic gel is about 7 to 10 wt%.

8. An electrode according to claim 1, wherein the linear polyethylene oxide has a molecular weight of about $0.2$ to $6 \times 10^6$ Daltons.

9. An electrode according to claim 1, wherein the face of the sheet adapted for interfacing with the patient's skin is covered by a backing sheet which is peelably removable therefrom.

10. An electrode according to claim 1, wherein the hydrophilic gel contains immersed therein a low area-weight scrim; wherein the water soluble salt is present in a concentration of about 0.1 to 15 wt%; wherein the linear polyethylene oxide has a molecular weight of about $0.5$ to $5 \times 10^6$ Daltons and is present in the hydrogel at a concentration of about 4 to 25%; and wherein the face of the sheet adapted for interfacing with the patient's skin is covered by a backing sheet which is peelably removable therefrom.

11. An electrode according to claim 10, wherein the scrim is formed of a sheet of non-woven polyethylene and wherein the water soluble salt is magnesium acetate.

* * * * *